(12) United States Patent
Kunz et al.

(10) Patent No.: US 9,637,510 B2
(45) Date of Patent: *May 2, 2017

(54) METHODS FOR PREPARING RUTHENIUM CARBENE COMPLEX PRECURSORS AND RUTHENIUM CARBENE COMPLEXES

(71) Applicant: Elevance Renewable Sciences, Inc., Woodridge, IL (US)

(72) Inventors: Linda A. Kunz, Woodridge, IL (US); Steven A. Cohen, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 109 days.

This patent is subject to a terminal disclaimer.

(21) Appl. No.: 14/610,519

(22) Filed: Jan. 30, 2015

(65) Prior Publication Data

US 2015/0210726 A1 Jul. 30, 2015

Related U.S. Application Data

(60) Division of application No. 13/606,640, filed on Sep. 7, 2012, now Pat. No. 8,975,414, which is a continuation-in-part of application No. 13/272,788, filed on Oct. 13, 2011, now Pat. No. 8,779,152.

(51) Int. Cl.
*C07F 15/00* (2006.01)

(52) U.S. Cl.
CPC ...... *C07F 15/0053* (2013.01); *C07F 15/0046* (2013.01)

(58) Field of Classification Search
CPC .................... C07F 15/0046; C07F 15/0053
See application file for complete search history.

(56) References Cited

U.S. PATENT DOCUMENTS

| 5,324,850 | A | 6/1994 | Juge et al. |
| 7,329,758 | B1 | 2/2008 | Grubbs et al. |
| 8,779,152 | B2 | 7/2014 | Kunz et al. |
| 2014/0323737 | A1* | 10/2014 | Kunz ............ C07F 15/0046 548/103 |

FOREIGN PATENT DOCUMENTS

EP 1 375 506 1/2004

OTHER PUBLICATIONS

Albers et al., Inorg. Syntheses, vol. 26, pp. 68-77 (1989).
Hallman et al., Inorg. Syntheses, vol. 12, pp. 237-240 (1970).
Bernardis et al., Reactive & Functonal Polymers, vol. 65, pp. 205-217 (2005).
Wilhelm et al., Organometallics, vol. 16, pp. 3867-3869 (1997).
Schwab et al., J. Am. Chem. Soc., vol. 118, pp. 100-110 (1996).
Deloume et al., Acta Cryst. B, vol. 35, pp. 558-561 (1979).
Emel'yanov et al., Zh. Strukt. Khim., vol. 49, pp. 585-588 (2008).
Weir et al., J. Chem. Thermodynamics, vol. 34, pp. 133-153 (2002).
Albers et al, Inorg. Syntheses, vol. 25, pp. 249-258 (1989).
Abstracts of CAPLUS Search Results (26 total pages).
Bellaloui et al., "Preparation and characterization of RuS2 . . . " C.R. Acad. Sci. Paris, t. 307, Series II, pp. 1171-1176 (1988) (part. trans.).
Scholl et al., Org. Lett., vol. 1, pp. 953-956 (1999).
Gmelins Handbuch der Anorganischen Chemie, pp. 82, 284-294, 302-312, and 426 (1970) (part. trans.).
Int'l Search Report for PCT App. No. PCT/US2012/059280, dated Jan. 22, 2013 (partial).
Linn et al., J. Chem. Ed., vol. 76, pp. 1484-1485 (1999).
Madec et al., Tetrahedron, vol. 57, pp. 2563-2568 (2001).
Schrodi et al., Aldrichimica Acta, vol. 40, pp. 45-52 (2007).
Colonial Metals, Product Information, copyright 2009, retrieved online Jun. 6, 2013, 7 pages.
Int'l Search Report and Written Opin. of Int'l Searching Authority for PCT App. No. PCT/US2012/059280, dated May 13, 2013.

* cited by examiner

*Primary Examiner* — Joseph Kosack
(74) *Attorney, Agent, or Firm* — Kilpatrick Townsend & Stockton LLP

(57) ABSTRACT

A method for preparing a ruthenium carbene complex precursor includes reacting a ruthenium refinery salt with a hydrogen halide to form a ruthenium intermediate, and reacting the ruthenium intermediate with an L-type ligand to form the ruthenium carbene complex precursor. A method for preparing a ruthenium vinylcarbene complex includes converting a ruthenium carbene complex precursor into a ruthenium hydrido halide complex, and reacting the ruthenium hydrido halide complex with a propargyl halide to form the ruthenium vinylcarbene complex. A method for preparing a ruthenium carbene complex includes converting a ruthenium carbene complex precursor into a ruthenium carbene complex having a structure $(PR^1R^2R^3)_2Cl_2Ru=CH-R^4$, wherein $R^1$, $R^2$, $R^3$, and $R^4$ are alike or different, and wherein covalent bonds may optionally exist between two or more of $R^1$, $R^2$, and $R^3$ and/or two of $R^1$, $R^2$, and $R^3$ taken together may optionally form a ring with phosphorous.

20 Claims, 7 Drawing Sheets

FIG. 2

REFINERY B SALT

$(NH_4)_2RuCl_5 \cdot H_2O$
$(NH_4)_4[Ru_2OCl_{10}]$
$NH_4Cl$ $\downarrow$ $-NH_4Cl$ $(NH_4)_2RuCl_5 \cdot H_2O$
$(NH_4)_4[Ru_2OCl_{10}]$

REFINERY A SALT

$(NH_4)_4[Ru_2OCl_{10}]$ $\searrow$ HCl  $\swarrow$ HCl $(NH_4)_2RuCl_6$ $\downarrow$ 1) 2 COD, EtOH, reflux, $N_2$
(optionally + reducing agent)
2) Wash with $H_2O$ $[RuCl_2(COD)]_x$

FIG. 4

REFINERY B SALT $(NH_4)_2RuCl_5 \cdot H_2O$
$(NH_4)_4[Ru_2OCl_{10}]$
$NH_4Cl$

↓ $-NH_4Cl$ $(NH_4)_2RuCl_5 \cdot H_2O$
$(NH_4)_4[Ru_2OCl_{10}]$

REFINERY A SALT $(NH_4)_4[Ru_2OCl_{10}]$

↘ HCl      ↙ HCl $(NH_4)_2RuCl_6$

↓ 3 $PPh_3$ (optionally + reducing agent)

$RuCl_2(PPh)_3$

METHODS FOR PREPARING RUTHENIUM CARBENE COMPLEX PRECURSORS AND RUTHENIUM CARBENE COMPLEXES

RELATED APPLICATIONS

This is a continuation-in-part of prior application Ser. No. 13/272,788, filed Oct. 13, 2011, the entire contents of which are incorporated herein by reference, except that in the event of any inconsistent disclosure or definition from the present specification, the disclosure or definition herein shall be deemed to prevail.

TECHNICAL FIELD

The present teachings relate generally to ruthenium carbene complex precursors and preparations thereof, as well as to the use of such precursors in the preparation of ruthenium carbene complexes.

BACKGROUND

With the development of new, relatively air-stable transition metal carbene complex catalysts—particularly ones exhibiting increased tolerance towards common organic functional groups—the olefin metathesis reaction has established itself as one of the most powerful reactions in the synthetic preparation of alkenes.

Ruthenium carbene complexes—for example, the "first-generation" and "second generation" Grubbs-type catalysts developed by Nobel laureate Robert H. Grubbs—are especially popular and versatile catalysts for use in olefin metathesis. The polymeric di-μ-chloro($\eta^4$-1,5-cyclooctadiene)ruthenium(II)—represented herein as $[RuCl_2(COD)]_x$—and the monomeric tris(triphenylphosphine)ruthenium(II) chloride—represented herein as $RuCl_2(PPh_3)_3$—are precursors in the synthesis of ruthenium carbene complexes.

As shown in FIG. 1, $[RuCl_2(COD)]_x$ (*Inorganic Syntheses*, 1989, 29, 68-77) and $RuCl_2(PPh_3)_3$ (*Inorganic Syntheses*, 1970, 12, 237-240) are typically prepared starting from $RuCl_3 \cdot nH_2O$. The ruthenium trichloride is itself prepared starting from ruthenium refinery salts (e.g., salts of ruthenium-halo complexes produced in the refining of natural platinum group metal deposits and recycled platinum group metals). However, since the ruthenium refinery salts are first converted to ruthenium metal, which in turn is then oxidized to Ru(III), the preparations of $[RuCl_2(COD)]_x$ and $RuCl_2(PPh_3)_3$ via the intermediacy of ruthenium trichloride are costly and inefficient.

A more efficient and less costly preparation of $[RuCl_2(COD)]_x$, $RuCl_2(PPh_3)_3$, and analogous $MX_2L_q$ ruthenium carbene complex precursors from ruthenium refinery salts—particularly one that does not require the intermediacy of ruthenium metal and/or ruthenium trichloride—is desirable.

SUMMARY

The scope of the present invention is defined solely by the appended claims, and is not affected to any degree by the statements within this summary.

By way of introduction, a first method for preparing a ruthenium carbene complex precursor in accordance with the present teachings includes (a) reacting a ruthenium refinery salt with a hydrogen halide to form a ruthenium intermediate, and (b) reacting the ruthenium intermediate with an L-type ligand and a reducing agent to form the ruthenium carbene complex precursor.

A second method for preparing a ruthenium carbene complex precursor in accordance with the present teachings includes (a) reacting a ruthenium refinery salt with a hydrogen halide to form a ruthenium intermediate, and (b) reacting the ruthenium intermediate with (i) cyclooctadiene and/or a phosphorous-containing material having a structure $PR^1R^2R^3$ and (ii) a reducing agent to form the ruthenium carbene complex precursor. The ruthenium refinery salt includes a material selected from the group consisting of $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, and combinations thereof. The ruthenium intermediate includes a compound selected from the group consisting of $(NH_4)_2RuX^1_6$, $(NH_4)_2RuX^1_yX^2_{6-y}$, wherein y is an integer value from 1 to 5, and a combination thereof. The reducing agent includes a metal selected from the group consisting of Group 7 elements, Group 8 elements, Group 9 elements, Group 10 elements, Group 11 elements, and combinations thereof. The ruthenium carbene complex precursor includes a compound having a structure $[RuX^3X^4(COD)]_x$, wherein x is an integer value of 1 or more, and/or a compound having a structure $RuX^5X^6(PR^1R^2R^3)_3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. Covalent bonds may optionally exist between two or more of $R^1$, $R^2$, and $R^3$; and two of $R^1$, $R^2$, and $R^3$ taken together may optionally form a ring with phosphorous. $X^1$, $X^2$, $X^3$, $X^4$, $X^5$, and $X^6$ are halogen atoms that are each independently selected from the group consisting of F, Cl, Br, and I with a caveat that $X^1$ and $X^2$ are different.

A first method for preparing a ruthenium vinylcarbene complex in accordance with the present teachings includes (a) converting a ruthenium carbene complex precursor prepared according to a method described above into a ruthenium hydrido halide complex, and (b) reacting the ruthenium hydrido halide complex with a propargyl halide to form the ruthenium vinylcarbene complex.

A method for preparing a ruthenium carbene complex in accordance with the present teachings includes converting a ruthenium carbene complex precursor prepared according to a method described above into a ruthenium carbene complex having a structure $(PR^1R^2R^3)_2X^1X^2Ru=CH-R^4$. $X^1$ and $X^2$ are halogen atoms that are each independently selected from the group consisting of F, Cl, Br, and I. $R^1$, $R^2$, $R^3$, and $R^4$ are alike or different, and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. Covalent bonds may optionally exist between two or more of $R^1$, $R^2$, and $R^3$, and/or two of $R^1$, $R^2$, and $R^3$ taken together may optionally form a ring with phosphorous.

A method of preparing an $MX_2L_q$ complex in accordance with the present teachings includes reacting a ruthenium (IV) hexahalo complex that includes a $[RuX^1_yX^2_{6-y}]^{2-}$ anion with an L-type ligand and a reducing agent, wherein y is an integer value from 1 to 6. The M includes ruthenium. $X^1$ and $X^2$ are halogen atoms that are independently selected from the group consisting of F, Cl, Br, and I.

BRIEF DESCRIPTION OF THE DRAWINGS

FIG. 2 shows a synthetic scheme for converting ruthenium refinery salts to [RuCl$_2$(COD)]$_x$ in accordance with the present teachings.

FIG. 4 shows a synthetic scheme for converting ruthenium refinery salts to RuCl$_2$(PPh$_3$)$_3$ in accordance with the present teachings.

DETAILED DESCRIPTION

Figure 1:
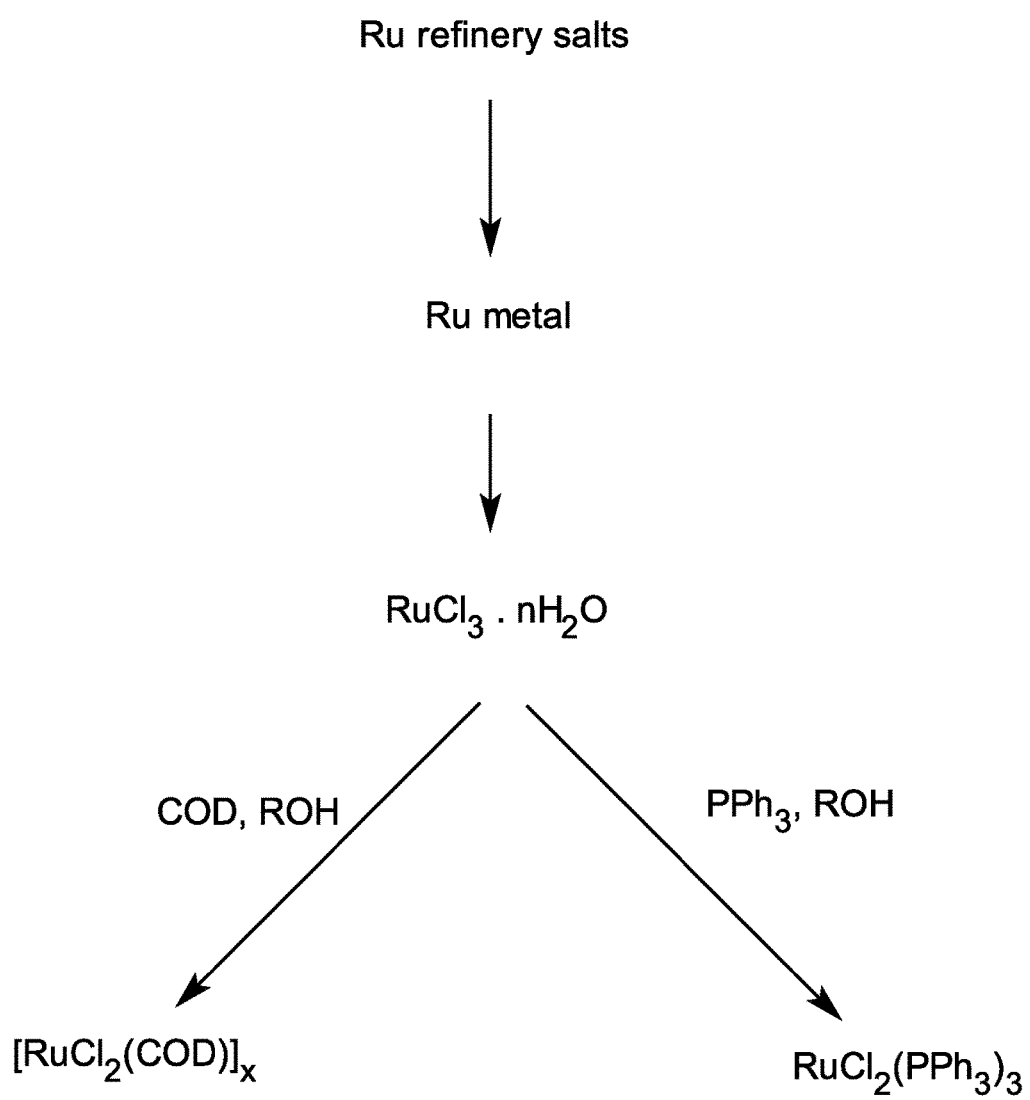
FIG. 1 shows a synthetic scheme for converting ruthenium refinery salts to $[RuCl_2(COD)]_x$ and $RuCl_2(PPh_3)_3$ by conventional methodologies.

A facile synthetic route to ruthenium carbene complex metathesis catalyst precursors—such as [RuCl$_2$(COD)]$_x$, RuCl$_2$(PPh$_3$)$_3$, and analogous MX$_2$L$_q$ complexes (e.g., where q is an integer from 1 through 4)—has been discovered and is described herein. As shown in FIGS. 2 and 4, the inventive route starts from low-cost ruthenium refinery salts and does not require any conversion of these salts to ruthenium metal or subsequent oxidation of ruthenium metal to RuCl$_3$—two of the principal drawbacks associated with the conventional synthetic preparations of [RuCl$_2$(COD)]$_x$, RuCl$_2$(PPh$_3$)$_3$, and analogous complexes.

Definitions

Throughout this description and in the appended claims, the following definitions are to be understood:

The phrase "ruthenium carbene complex precursor" refers generally to any ruthenium complex useful in the preparation of various ruthenium reagents and/or catalyst compositions, including but not limited to carbene complexes.

The phrase "ruthenium refinery salt" refers generally to a ruthenium- and halogen-containing material. It is to be understood that a "ruthenium refinery salt" as defined herein may further comprise additional elements besides ruthenium and halogen, including but not limited to oxygen. Representative examples of "ruthenium refinery salts" include but are not limited to materials obtained from—or substantially chemically equivalent to what could otherwise be obtained from—the processing of a natural platinum group metal (PGM) deposit, as well as materials obtained from alternative chemical sources (e.g., ammoniated ruthenium oxychloride a.k.a. ruthenium red, etc.) and/or from recovery and/or reclamation processing of a ruthenium-containing material used in a prior chemical reaction. In some embodiments, a "ruthenium refinery salt" is obtained from a natural PGM deposit by a technique as described in *Reactive & Functional Polymers*, 2005, 65, 205-217.

The phrase "ruthenium intermediate" refers to a ruthenium-containing material that is obtained from but is chemically different than a ruthenium refinery salt that was subjected to a reaction involving a hydrogen halide.

The phrase "L-type ligand" refers to a two-electron neutral ligand. Representative examples of an "L-type ligand" for use in accordance with the present teachings include but are not limited to olefins, phosphines, phosphites, amines, carbon monoxide (CO), nitrogen (N$_2$), and the like, and combinations thereof.

The term "olefin" refers to a hydrocarbon compound containing at least one carbon-carbon double bond. As used herein, the term "olefin" encompasses straight, branched, and/or cyclic hydrocarbons having only one carbon-carbon double bond (e.g., monoenes) as well as more than one carbon-carbon double bond (e.g., dienes, trienes, etc.). In some embodiments, the olefin is functionalized.

The term "functionalized" as used in reference to an olefin refers to the presence of one or more heteroatoms, wherein the heteroatom is an atom other than carbon and hydrogen. In some embodiments, the heteroatom constitutes one atom of a polyatomic functional group with representative functional groups including but not limited to carboxylic acids, carboxylic esters, ketones, aldehydes, anhydrides, sulfur-containing groups, phosphorous-containing groups, amides, imides, N-containing heterocycles, aromatic N-containing heterocycles, salts thereof, and the like, and combinations thereof.

The term "hydrothermal" used in connection with reactions, conversions, treatments, and the like refers to reaction conditions within a substantially "closed" reaction system—typically though not necessarily a system in which pressure and/or temperature exceed atmospheric conditions—such as may be achieved in a Parr-type reactor.

The term "atmospheric" used in connection with reactions, conversions, treatments, and the like refers to reaction conditions within an "open" (as opposed to closed) reaction system. It is to be understood that "atmospheric" in the sense used herein does not preclude the introduction into a reaction vessel of an inert atmosphere (e.g., a blanket of an inert gas) to replace or exclude air. Moreover, it is to be further understood that in an open reaction system, an internal temperature and/or pressure within the reaction vessel may exceed the ambient temperature and/or pressure outside the reaction vessel (in other words, "atmospheric" as used herein is not necessarily synonymous with "ambient" although, in some embodiments, it may be).

It is to be understood that elements and features of the various representative embodiments described below may be combined in different ways to produce new embodiments that likewise fall within the scope of the present teachings.

By way of general introduction, a method for preparing a ruthenium carbene complex precursor in accordance with the present teachings comprises reacting a ruthenium refinery salt with a hydrogen halide to form a ruthenium intermediate, and reacting the ruthenium intermediate with an L-type ligand to form the ruthenium carbene complex precursor. In some embodiments, as further described below, a reducing agent is optionally provided in the reaction of the ruthenium intermediate with the L-type ligand.

In some embodiments, the hydrogen halide is provided as a gas. In some embodiments, the hydrogen halide is provided in solution. In some embodiments, the hydrogen halide is provided as an aqueous solution. In some embodiments, the hydrogen halide is selected from the group consisting of hydrogen chloride, hydrogen bromide, hydrogen fluoride, hydrogen iodide, and combinations thereof. In some embodiments, the hydrogen halide is selected from the group consisting of hydrogen chloride, hydrogen bromide, hydrogen iodide, and combinations thereof. In some embodiments, the hydrogen halide is selected from the group consisting of hydrogen chloride, hydrogen bromide, and a combination thereof. In some embodiments, the hydrogen halide comprises hydrogen chloride. In some embodiments, the hydrogen halide comprises an aqueous solution of hydrogen chloride (e.g., hydrochloric acid). In some embodiments, the hydrogen halide comprises hydrogen bromide. In some embodiments, the hydrogen halide comprises an aqueous solution of hydrogen bromide (e.g., hydrobromic acid).

In some embodiments, the L-type ligand is selected from the group consisting of olefins, phosphines, phosphites, amines, CO, $N_2$, and combinations thereof. In some embodiments, the L-type ligand is selected from the group consisting of olefins, phosphines, and a combination thereof.

In some embodiments, the L-type ligand comprises an olefin. In some embodiments, the olefin is selected from the group consisting of monoenes, dienes, trienes, and combinations thereof. In some embodiments, the olefin is acyclic. In some embodiments, the olefin comprises an acyclic $C_6$ or greater monoene. In some embodiments, the olefin comprises an acyclic diene with representative acyclic dienes including but not limited to 1,5-hexadiene, 2,6-octadiene, and the like, and combinations thereof. In some embodiments, the olefin is cyclic. In some embodiments, the olefin comprises a cyclic diene with representative cyclic dienes including but not limited to cyclopentadiene, cyclohexadiene, cycloheptadiene, cyclooctadiene, cyclononadiene, cyclodecadiene, cycloundecadiene, cyclododecadiene, paramenthadiene, phellandrene, norbornadiene, terpinene, limonene, and the like, and combinations thereof. In some embodiments, the olefin comprises an acyclic triene. In some embodiments, the olefin comprises a cyclic triene with a representative cyclic triene including but not limited to cyclododecatriene. In some embodiments, the olefin is aromatic with representative aromatic olefins including but not limited to cyclopentadienyl, benzene, toluene, o-xylene, m-xylene, p-xylene, mesitylene, and the like, and combinations thereof.

In some embodiments, the L-type ligand comprises a phosphorous-containing ligand (e.g., phosphines, phosphites, and the like, and combinations thereof). In some embodiments, the phosphorous-containing ligand comprises a structure $PR^1R^2R^3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorous. In some embodiments, the phosphorous-containing ligand comprises a phosphine. In some embodiments, the phosphine comprises a trialkyl phosphine. In some embodiments, the phosphine comprises triphenyl phosphine. In some embodiments, the phosphorous-containing ligand comprises a phosphite.

The chemical composition of a particular ruthenium refinery salt for use in accordance with the present teachings can differ according to the specific process used to generate it, the refinery that produced it, and/or the exact methodology used to separate the ruthenium from a natural PGM deposit or recovered PGM source. Moreover, it is to be understood that a ruthenium refinery salt in accordance with the present teachings can include one or more impurities—including but not limited to Ru metal, $NH_4Cl$, and the like, and combinations thereof—that are either removed, either partially or completely, prior to reacting the ruthenium refinery salt with hydrogen halide, or else carried along, either in whole or in part, for the reaction with hydrogen halide. For embodiments in which one or more impurity (e.g., Ru metal, $NH_4Cl$, etc.) is not completely removed from the ruthenium refinery salt prior to reacting the ruthenium refinery salt with hydrogen halide, at least a portion of the one or more impurity may be carried over into the resultant ruthenium intermediate which, in some embodiments, may itself be further contaminated by the presence of unreacted starting material (e.g., $(NH_4)_4[Ru_2OCl_{10}]$, etc.). In such instances, the one or more impurity and/or unreacted starting material can be removed, either partially or completely, prior to reacting the ruthenium intermediate with an L-type ligand to form the ruthenium carbene complex precursor or else carried along, either in whole or in part, for the reaction with an L-type ligand.

In some embodiments, a ruthenium refinery salt in accordance with the present teachings comprises one or a plurality of halide ligands and/or one or a plurality of cations. In some embodiments, the ruthenium refinery salt comprises one or a plurality of ammonium cations. In some embodiments, the ruthenium refinery salt comprises one or a plurality of different cations (e.g., alkali metal cations, including but not limited to potassium and sodium, etc.) instead of or in addition to one or a plurality of ammonium cations. In some embodiments, a ruthenium refinery salt in accordance with the present teachings comprises one or a plurality of chloride ligands and/or one or a plurality of ammonium cations. In some embodiments, a ruthenium refinery salt for use in accordance with the present teachings is one produced by Refinery A. In some embodiments, the ruthenium refinery salt is one produced by Refinery B. In some embodiments, the ruthenium refinery salt is a combination of a material produced by Refinery A and a material produced by Refinery B.

As further described in Examples 1 and 2 below, x-ray powder diffraction (XRD) analysis of representative ruthenium refinery salts purchased, respectively, from Refinery A and Refinery B was performed. The XRD analysis of a representative ruthenium refinery salt obtained from Refinery B revealed the following composition: $(NH_4)_4[Ru_2OCl_{10}]$ (36.4 wt %), $(NH_4)_2RuCl_5.H_2O$ (13.9 wt %), and $NH_4Cl$ (49.3 wt %). By contrast to the large weight percentage of $NH_4Cl$ impurity identified in the Refinery B sample, an XRD analysis of a representative ruthenium refinery salt obtained from Refinery A revealed the following composition: $(NH_4)_4[Ru_2OCl_{10}]$ (96.1 wt %) and Ru metal impurity (3.9 wt %).

In some embodiments, a ruthenium refinery salt for use in accordance with the present teachings comprises a material selected from the group consisting of $(NH_4)_2RuCl_5$, $(NH_4)_2RuCl_5.H_2O$, polyhydrated $(NH_4)_2RuCl_5$, $(NH_4)_4[Ru_2OCl_{10}]$, and combinations thereof. In some embodiments, a ruthenium refinery salt for use in accordance with the present teachings comprises $(NH_4)_4[Ru_2OCl_{10}]$. In some embodiments, the ruthenium refinery salt further comprises an $NH_4Cl$ impurity which, in some embodiments, is residual reagent left over from a ruthenium recovery process (e.g., when $NH_4Cl$ is added to solution to precipitate pentachloro ruthenium species).

In some embodiments, the method in accordance with the present teachings further comprises removing at least a portion of the excess $NH_4Cl$ (if present) from the ruthenium refinery salt prior to reacting the ruthenium refinery salt with the hydrogen halide. Although pre-removal of excess $NH_4Cl$ is not essential, in some embodiments it is desirable inasmuch as higher yields are generally achievable when excess $NH_4Cl$ has been removed. In some embodiments, at least a portion of the $NH_4Cl$ impurity is removed via sublimation. In some embodiments, at least a portion of sublimed $NH_4Cl$ is removed from the remaining ruthenium refinery salt prior to reacting the remaining ruthenium refinery salt with the hydrogen halide. In some embodiments, at least a portion of the $NH_4Cl$ impurity is removed by washing—for example, with water and/or alcohol (e.g., ethanol, butanol, etc.)—such as in a flask or a Soxhlet extractor at ambient or elevated temperature.

In some embodiments, the ruthenium refinery salt used in accordance with the present teachings is a Refinery A sample inasmuch as it does not contain a significant amount of $NH_4Cl$ impurity that would warrant the extra step of its removal. It is to be understood that while the methods described herein have been demonstrated using ruthenium refinery salts from two different refineries—Refinery A and Refinery B—the present teachings can also be applied to ruthenium refinery salts from other refineries as well without limitation.

In some embodiments, the reacting of a ruthenium refinery salt with a hydrogen halide to form a ruthenium intermediate comprises a hydrothermal treatment. In some embodiments, the reacting is performed in a closed system. In some embodiments, a reaction temperature in the closed system is at least about 100° C. In some embodiments, a reaction temperature in the closed system is at least about 120° C. In some embodiments, a reaction temperature in the closed system is at least about 130° C. In some embodiments, a reaction temperature in the closed system is at least about 140° C. In some embodiments, a reaction temperature in the closed system is at least about 150° C. In some embodiments, a reaction temperature in the closed system is at least about 160° C. In some embodiments, a reaction temperature in the closed system is at least about 170° C. In some embodiments, a reaction temperature in the closed system is at least about 175° C. In some embodiments, a reaction temperature in the closed system is at least about 180° C.

Although the use of a gaseous hydrogen halide has been contemplated for some embodiments of the present teachings (for both hydrothermal and atmospheric conversions of ruthenium refinery salt to ruthenium intermediate), it is presently believed that the use of gaseous reagent may be less practical and/or slower than the use of a corresponding liquid acid reagent. Thus, in some embodiments, the hydrogen halide is provided in solution. In some embodiments, the hydrogen halide is provided in an aqueous solution.

In some embodiments, the hydrogen halide comprises hydrogen chloride which, in some embodiments, is provided in aqueous solution as hydrochloric acid. In some embodiments, the hydrochloric acid has a concentration of at least about 3M or higher. In some embodiments, the hydrochloric acid has a concentration of at least about 4M or higher. In some embodiments, the hydrochloric acid has a concentration of at least about 5M or higher. In some embodiments, the hydrochloric acid has a concentration of at least about 6M or higher. In some embodiments, the hydrochloric acid has a concentration of at least about 7M or higher. In some embodiments, the hydrochloric acid has a concentration of at least about 8M or higher. In some embodiments, the hydrochloric acid has a concentration of at least about 9M or higher. In some embodiments, the hydrochloric acid is concentrated hydrochloric acid.

In some embodiments, the hydrogen halide comprises hydrogen bromide which, in some embodiments, is provided in aqueous solution as hydrobromic acid. In some embodiments, the ruthenium intermediate formed by reacting a ruthenium refinery salt with hydrogen bromide comprises one or a plurality of ammonium cations and/or one or a plurality of bromide ligands. In some embodiments, the ruthenium intermediate comprises a compound having a structure $(NH_4)_2RuBr_6$. In some embodiments, the ruthenium intermediate comprises a compound having a structure $(NH_4)_2RuBr_6$ and/or $(NH_4)_2RuCl_zBr_{6-z}$, where z is an integer from 1 to 5.

While neither desiring to be bound by any particular theory nor intending to limit in any measure the scope of the appended claims or their equivalents, it is presently believed that the yield of the hydrothermal reaction by which ruthenium refinery salt is converted to ruthenium intermediate increases with increasing concentration of the acid (e.g., hydrochloric acid). In addition, in view of the water solubility of the ruthenium intermediate, it is presently believed that the yield can be improved by washing the solid ruthenium intermediate product with an organic solvent instead of water. Representative organic solvents for use in accordance with the present teachings include but are not limited to aliphatic hydrocarbons (e.g., pentane, hexane, heptane, cyclohexane, etc.), esters (e.g., diethyl acetate, etc.), ketones (e.g., acetone, etc.), alcohols (e.g., methanol, ethanol, isopropyl alcohol, etc.), aromatic hydrocarbons (e.g., benzene, toluene, xylenes, etc.), halogenated aromatic hydrocarbons (e.g., chlorobenzene, dichlorobenzene, etc.), halogenated alkanes (e.g., dichloromethane, chloroform, dichloroethane, etc.), ethers (e.g., dioxane, tetrahydrofuran, diethyl ether, tert-butyl methyl ether, dimethoxyethane, etc.), and the like, and combinations thereof. In some embodiments, the organic solvent used to wash the solid ruthenium intermediate product is cooled below room temperature prior to being used for the washing. In some embodiments, the organic solvent comprises acetone.

In some embodiments, the ruthenium refinery salt is one that is obtained from Refinery A, which was predetermined by XRD analysis to contain about 96.1 wt % $(NH_4)_4[Ru_2OCl_{10}]$ and about 3.9 wt % Ru metal impurity. In some embodiments, the Refinery A ruthenium refinery salt is converted to a ruthenium intermediate comprising $(NH_4)_2RuCl_6$—which, in some embodiments, appears as black crystals—via a hydrothermal treatment (150° C., 9M HCl, 1.5 h) in yields of about 90 to about 95 percent (with about 4% of byproduct recovered by weight).

In some embodiments, the ruthenium refinery salt is one that is obtained from Refinery B, which was predetermined by XRD analysis to contain about 36.4 wt % $(NH_4)_4[Ru_2OCl_{10}]$, about 13.9 wt % $(NH_4)_2RuCl_5.H_2O$, and about 49.3 wt % $NH_4Cl$ impurity. In some embodiments, excess $NH_4Cl$ (about 40 wt %) is first removed from the Refinery B ruthenium refinery salt via sublimation. In some embodiments, the Refinery B ruthenium refinery salt remaining after sublimation is converted to a ruthenium intermediate comprising $(NH_4)_2RuCl_6$—which, in some embodiments, appears as black crystals—via a hydrothermal treatment (150° C., 9M HCl, 2 h) in yields of about 82 to about 95 percent.

In some embodiments, the reacting of a ruthenium refinery salt with hydrogen halide to form a ruthenium intermediate comprises atmospheric conditions. In some embodiments, the reacting is performed in an open system. In some embodiments, the reacting is performed in an open system and the hydrogen halide is provided as an aqueous solution. In some embodiments, the hydrogen halide comprises hydrogen chloride, which in some embodiments is provided in aqueous solution as hydrochloric acid. In some embodiments, the hydrogen chloride is provided in aqueous solution as concentrated hydrochloric acid. In some embodiments, the hydrochloric acid has a concentration of at least about 6M or higher. In some embodiments, the hydrochloric acid has a concentration of at least about 7M or higher. In some embodiments, the hydrochloric acid has a concentration of at least about 8M or higher. In some embodiments, the hydrochloric acid has a concentration of at least about 9M or higher. In some embodiments, the reacting comprises refluxing the ruthenium refinery salt in concentrated hydrochloric acid. In some embodiments, the hydrogen halide comprises hydrogen bromide, which in some embodiments is provided in aqueous solution as hydrobromic acid. In some embodiments, the reacting comprises refluxing the ruthenium refinery salt in concentrated hydrobromic acid.

In some embodiments, the reacting under atmospheric conditions comprises refluxing the ruthenium refinery salt in an aqueous solution of a hydrogen halide. In some embodiments, the reacting under atmospheric conditions comprises refluxing the ruthenium refinery salt in hydrochloric acid (e.g., 7M, 8M, 9M or concentrated) for at least 5 hours, in some embodiments for at least 6 hours, and in some embodiments for at least 7 or more hours. In some embodiments, the ruthenium intermediate obtained by the atmospheric synthesis is a black solid. However, the ruthenium intermediate product produced under atmospheric conditions does not always appear to be black. In some embodiments, the yields of ruthenium intermediate obtained by atmospheric synthesis are about 80 to about 90 percent.

Either atmospheric or hydrothermal conditions can be used for the conversion of a ruthenium refinery salt to a ruthenium intermediate in accordance with the present teachings. In some embodiments, hydrothermal conditions may be desirable (e.g., to increase reproducibility of the conversion). In some embodiments, atmospheric conditions may be desirable (e.g., in larger scale reactions for which an appropriately sized Parr-type reactor is not readily available).

In some embodiments, the ruthenium intermediate formed from the reaction of a ruthenium refinery salt with hydrogen halide comprises one or a plurality of ammonium cations and/or one or a plurality of halide ligands. In some embodiments, the hydrogen halide comprises hydrogen chloride, and the ruthenium intermediate formed from the reaction of a ruthenium refinery salt with hydrogen chloride comprises one or a plurality of ammonium cations and/or one or a plurality of chloride ligands. In some embodiments, the ruthenium intermediate further comprises one or a plurality of additional halide ligands other than chloride. In some embodiments, the ruthenium intermediate comprises a compound selected from the group consisting of $(NH_4)_2RuCl_6$, $(NH_4)_3RuCl_6$, $(NH_4)_2RuCl_5 \cdot H_2O$, $(NH_3)_6RuCl_3$, $(NH_4)_2RuBr_6$, $(NH_4)_2RuCl_zBr_{6-z}$, wherein z is an integer from 1 to 5, and combinations thereof.

In some embodiments, the ruthenium intermediate comprises a compound selected from the group consisting of $(NH_4)_2RuCl_6$, $(NH_4)_2RuBr_6$, $(NH_4)_2RuCl_zBr_{6-z}$, wherein z is an integer from 1 to 5, and combinations thereof. In some embodiments, the ruthenium intermediate comprises a compound having a structure $(NH_4)_2RuCl_6$. In some embodiments, at least a portion of the $(NH_4)_2RuCl_6$ appears as crystalline. In other embodiments, at least a portion of the $(NH_4)_2RuCl_6$ appears as a powder. In some embodiments, the $(NH_4)_2RuCl_6$ appears as black microcrystals. While neither desiring to be bound by any particular theory nor intending to limit in any measure the scope of the appended claims or their equivalents, it is presently believed that at least a portion of the $(NH_4)_2RuCl_6$ appears as crystalline when it has been prepared according to hydrothermal conditions, whereas at least a portion of the $(NH_4)_2RuCl_6$ appears as a powder when it has been prepared according to atmospheric conditions.

As further described in Example 15 below, samples of ruthenium intermediates obtained from the hydrothermal and atmospheric treatments of a ruthenium refinery salt with hydrochloric acid were examined by XRD analysis and were found to be comprised primarily of $(NH_4)_2RuCl_6$. Depending on the conditions under which the ruthenium intermediate was formed, the samples were found to contain varying amounts of impurities including $(NH_4)_4[Ru_2OCl_{10}]$ and Ru metal.

In some embodiments, the ruthenium intermediate obtained from the hydrothermal and/or atmospheric treatment of a ruthenium refinery salt in accordance with the present teachings is reacted with an olefin to form a ruthenium carbene complex precursor. In some embodiments, the olefin is cyclic. In some embodiments, the cyclic olefin is selected from the group consisting of cyclohexadiene, cycloheptadiene, cyclooctadiene, cyclononadiene, cyclodecadiene, cycloundecadiene, cyclododecadiene, cyclododecatriene, all stereoisomers thereof, and the like, and combinations thereof. In some embodiments, the cyclic olefin is selected from the group consisting of cyclooctadiene, cyclododecatriene, and combinations thereof.

In some embodiments, about two equivalents of a cyclic olefin are reacted with a ruthenium intermediate to form a ruthenium carbene complex precursor in accordance with the present teachings. In some embodiments, about two equivalents of cyclooctadiene are reacted with a ruthenium intermediate to form a ruthenium carbene complex precursor in accordance with the present teachings. In some embodiments, the olefin (e.g., cyclooctadiene) is reacted with the ruthenium intermediate in an alcoholic solvent which, in some embodiments, can further serve as a reducing agent. Representative alcoholic solvents include but are not limited to aliphatic alcohols (e.g., methanol, ethanol, 1-propanol, iso-propanol, 1-butanol, sec-butanol, and the like, and combinations thereof), aromatic alcohols, polyols, and the like, and combinations thereof. In some embodiments, the cyclooctadiene reacted with the ruthenium intermediate comprises cis, cis-1,5-cyclooctadiene. In some embodiments, the ruthenium intermediate comprises $(NH_4)_2RuCl_6$, the cyclooctadiene comprises cis, cis-1,5-cyclooctadiene, and the reacting comprises refluxing the $(NH_4)_2RuCl_6$ and cis, cis-1,5-cyclooctadiene in an aliphatic alcoholic solvent. In some embodiments, the reaction of the ruthenium intermediate with cis, cis-1,5-cyclooctadiene to form a ruthenium carbene complex precursor is conducted in ethanol. In some embodiments, the yield of the reaction is higher in ethanol than in butanol, methanol or iso-propanol.

In some embodiments, a ruthenium intermediate $(NH_4)_2RuCl_6$ prepared under hydrothermal conditions is reacted with cyclooctadiene to form a ruthenium carbene complex precursor. In other embodiments, a ruthenium intermediate $(NH_4)_2RuCl_6$ prepared under atmospheric conditions is reacted with cyclooctadiene to form a ruthenium carbene complex precursor. While neither desiring to be bound by any particular theory nor intending to limit in any measure the scope of the appended claims or their equivalents, it is presently observed that (a) the yield of ruthenium carbene complex precursor from the reaction of ruthenium intermediate with cyclooctadiene increases (e.g., from about 33% to about 62%) as reaction time increases (e.g., from about 7 hours to about 30 hours), (b) the yield of the ruthenium carbene complex precursor does not change significantly when the amount of cyclooctadiene is increased from 2 equivalents to 3 equivalents, (c) using a ruthenium intermediate $(NH_4)_2RuCl_6$ prepared under hydrothermal conditions yields the same ruthenium carbene complex precursor as does using a ruthenium intermediate $(NH_4)_2RuCl_6$ prepared under atmospheric conditions, and (d) the reaction between ruthenium intermediate and cyclooctadiene proceeds to the same yield regardless of whether it is conducted in air or in a nitrogen atmosphere.

In some embodiments, as shown in FIG. 2, the ruthenium carbene complex precursor comprises a material having a structure $[RuCl_2(COD)]_x$, wherein x is an integer value of 1 or more. In some embodiments, the $[RuCl_2(COD)]_x$ is polymeric. In some embodiments, the $[RuCl_2(COD)]_x$ appears as a yellowish-brownish solid.

Figure 3:
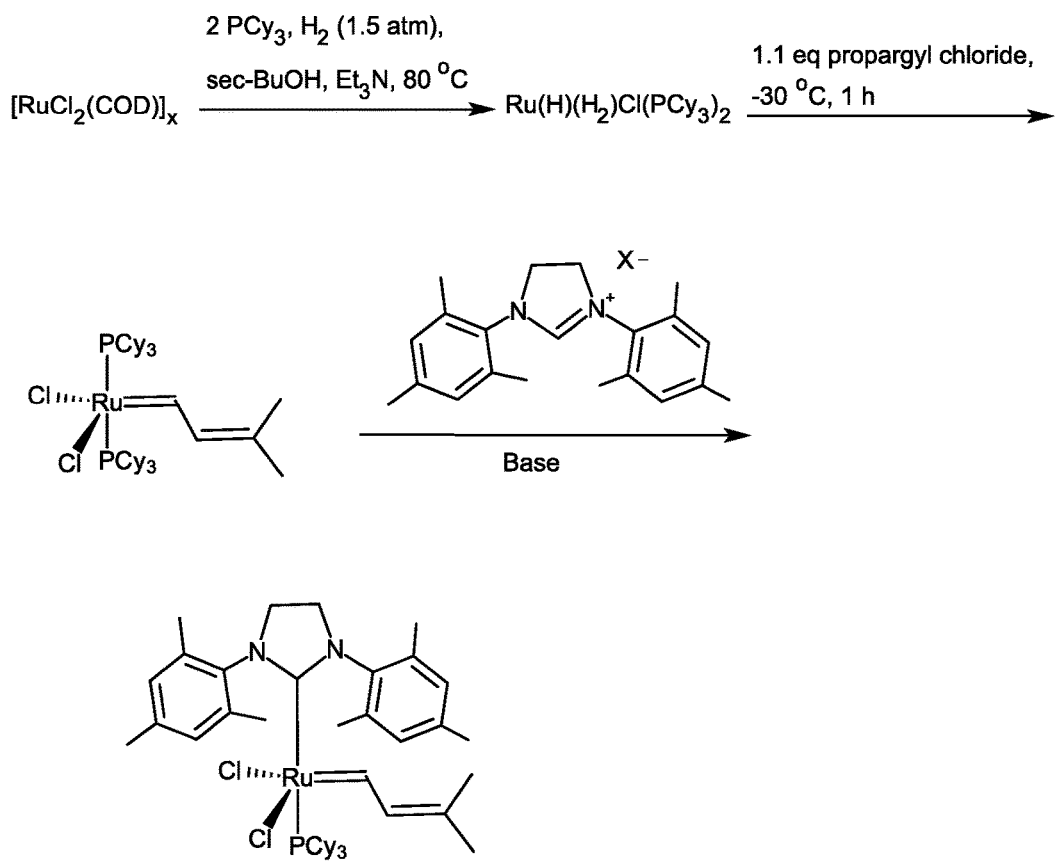
FIG. 3 shows a synthetic scheme for converting the ruthenium carbene complex precursor [RuCl$_2$(COD)]$_x$ to a ruthenium carbene compound for use as an olefin metathesis catalyst.

In some embodiments, as shown in FIG. 3, a method for preparing a ruthenium vinylcarbene complex comprises converting a ruthenium carbene complex precursor prepared in accordance with the present teachings into a ruthenium hydrido halide complex, and reacting the ruthenium hydrido halide complex with a propargyl halide to form the ruthenium vinylcarbene complex. In some embodiments, the vinylcarbene complex constitutes a first-generation Grubbs-type olefin metathesis catalyst. In some embodiments, as shown in FIG. 3, the converting of the ruthenium carbene complex precursor into the ruthenium hydrido halide complex comprises reacting the ruthenium carbene complex precursor with a trialkyl phosphine, hydrogen, and a trialkyl amine as described, for example, in *Organometallics,* 1997, 16, No. 18, 3867-3869.

In some embodiments, the ruthenium hydrido halide complex comprises a compound having a structure $[Ru(H)(H_2)X(PR^1R^2R^3)_2]$, wherein X is a halide and wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorous. In some embodiments, the $C_1$-$C_{10}$ alkyl group is primary alkyl, secondary alkyl or cycloalkyl. In some embodiments, the cycloalkyl is cyclohexyl (Cy). In some embodiments, the ruthenium hydrido halide complex comprises a compound having a structure $[Ru(H)(H_2)Cl(PCy_3)_2]$. In some embodiments, the propargyl halide comprises 3-chloro-3-methyl-1-butyne. In some embodiments, as shown in FIG. 3, the ruthenium vinylcarbene complex prepared from the ruthenium carbene complex precursor comprises a compound having a structure $(PCy_3)_2Cl_2Ru=CH-CH=C(CH_3)_2$.

In some embodiments, the above-described method for preparing a ruthenium vinylcarbene complex further comprises replacing a phosphorous-containing ligand of the ruthenium vinylcarbene complex $[Ru(H)(H_2)X(PR^1R^2R^3)_2]$ with an N-heterocyclic carbene ligand as described, for example, in U.S. Pat. No. 7,329,758 B1. In some embodiments, a phosphorous-containing ligand of the ruthenium vinylcarbene complex (e.g., a trialkyl phosphine ligand) is replaced with an imidazolidine ligand to form an imidazolidine-containing ruthenium vinylcarbene complex. In some embodiments, as shown in FIG. 3, the imidazolidine ligand comprises 1,3-dimesityl-4,5-dihydroimidazole. In some embodiments, the imidazolidine-containing ruthenium vinylcarbene complex constitutes a second-generation Grubbs-type olefin metathesis catalyst.

In some embodiments, the ruthenium intermediate obtained from the hydrothermal and/or atmospheric treatment of a ruthenium refinery salt in accordance with the present teachings is reacted with a phosphorous-containing material (e.g., a phosphine and/or phosphite) to form a ruthenium carbene complex precursor. In some embodiments, the phosphorous-containing material comprises a structure $PR^1R^2R^3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorous. In some embodiments, one or more of $R^1$, $R^2$, and $R^3$ comprises phenyl. In some embodiments, each of $R^1$, $R^2$, and $R^3$ comprises phenyl. In some embodiments, one or more of $R^1$, $R^2$, and $R^3$ comprises cycloalkyl (e.g., cyclohexyl). In some embodiments, each of $R^1$, $R^2$, and $R^3$ comprises cycloalkyl (e.g., cyclohexyl). In some embodiments, the ruthenium intermediate obtained from the hydrothermal and/or atmospheric treatment of a ruthenium refinery salt with a hydrogen chloride in accordance with the present teachings is reacted with three equivalents of a phosphorous-containing material (e.g., a phosphine) to form a ruthenium carbene complex precursor comprising a structure $RuCl_2(PR^1R^2R^3)_3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorous.

Figure 5:
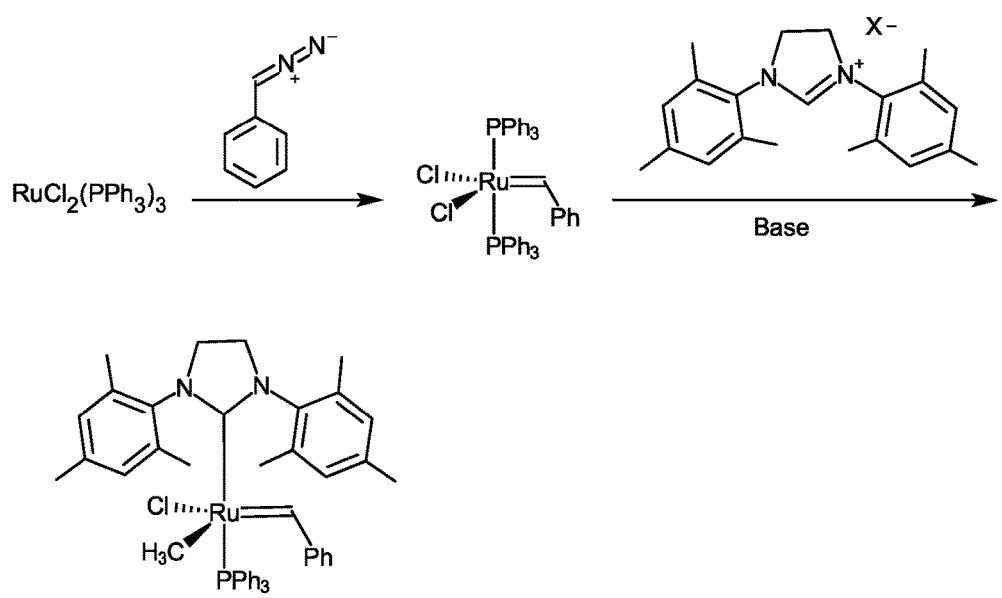
FIG. 5 shows a synthetic scheme for converting the ruthenium carbene complex precursor RuCl$_2$(PPh$_3$)$_3$ to a ruthenium carbene compound for use as an olefin metathesis catalyst.

In some embodiments, as shown in FIG. 5, a method for preparing a ruthenium carbene complex comprises converting a ruthenium carbene complex precursor prepared in accordance with the present teachings into a ruthenium carbene complex having a structure $(PR^1R^2R^3)_2Cl_2Ru=CH-R^4$, wherein $R^1$, $R^2$, $R^3$, and $R^4$ are alike or different, and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorous. In some embodiments, one or more of $R^1$, $R^2$, $R^3$, and $R^4$ comprises phenyl. In some embodiments, each of $R^1$, $R^2$, $R^3$, and $R^4$ comprises phenyl. In some embodiments, one or more of $R^1$, $R^2$, $R^3$, and $R^4$ comprises cycloalkyl (e.g., cyclohexyl). In some embodiments, each of $R^1$, $R^2$, $R^3$, and $R^4$ comprises cycloalkyl (e.g., cyclohexyl). In some embodiments, the carbene complex constitutes a first-generation Grubbs-type olefin metathesis catalyst. In some embodiments, as shown in FIG. 5, the converting of the ruthenium carbene complex precursor into a ruthenium carbene complex comprises reacting the ruthenium carbene complex precursor with phenyldiazomethane as described, for example, in *J. Am. Chem. Soc.,* 1996, 118, 100.

In some embodiments, as shown in FIG. 5, the above-described method for preparing a ruthenium carbene complex further comprises replacing a phosphorous-containing ligand of the ruthenium carbene complex (e.g., a phosphine) with an N-heterocyclic carbene ligand to form an N-heterocyclic carbene-containing ruthenium carbene complex. In some embodiments, a phosphorous-containing ligand of the ruthenium carbene complex is replaced with an imidazolidine ligand to form an imidazolidine-containing ruthenium carbene complex. In some embodiments, as shown in FIG. 5, the imidazolidine ligand comprises 1,3-dimesityl-4,5-dihydroimidazole. In some embodiments, the imidazolidine-containing ruthenium carbene complex constitutes a second-generation Grubbs-type olefin metathesis catalyst.

By way of illustration, as shown in FIGS. 3 and 5, ruthenium carbene complex precursors such as [RuCl$_2$(COD)]$_x$ and RuCl$_2$(PPh$_3$)$_3$ prepared in accordance with the present teachings can be readily transformed into ruthenium carbene complexes for use as olefin metathesis catalysts (e.g., first- and/or second-generation Grubbs-type metathesis catalysts). Moreover, in contrast to conventional methodology, the present teachings circumvent costly conversions of ruthenium refinery salts to ruthenium metal and subsequent oxidation of ruthenium metal to RuCl$_3$. In addition, the present teachings are in no way limited to the ruthenium feedstock from a particular refinery, and salts from other refineries or sources in addition to the A and B refineries referenced herein may be employed.

In an effort to increase the yield of ruthenium carbene complex precursor formed from the reaction of a ruthenium intermediate (e.g., one prepared by the hydrothermal and/or atmospheric treatment of a ruthenium refinery salt) and an L-type ligand in accordance with the present teachings, alternative reaction conditions were screened. The screening reactions were run for 7 hours (30% yield std.) to test different conditions, with the best conditions then being further tested in 24-hour reactions (62% yield std.). The conditions examined include the following: (1) solvent, which can act as a reducing agent to reduce Ru$^{4+}$ to Ru$^{2+}$ (e.g., methanol, ethanol, 1-propanol, iso-propanol, 1-butanol, 95:5 water:ethanol, etc.); (2) addition of H$_2$O (e.g., 0-4 eq.); (3) addition of phase transfer catalysts (e.g., decatrimethylammonium chloride, hexadecyltrimethylammonium chloride, etc.) to increase solubility of ruthenium refinery salts in alcoholic solvent; and (4) addition of reducing agents (e.g., organic and/or inorganic).

With respect to (1), the best yield was observed with ethanol as solvent. Thus, in some embodiments, the solvent for the reaction of a ruthenium intermediate with an L-type ligand in accordance with the present teachings comprises ethanol. With respect to (2) and (3), no significant increase in yield resulting from the addition of water or a phase transfer catalyst was observed in 24-hour reactions. With respect to (4), a large increase in yield was observed when FeCl$_2$ or CoCl$_2$ was added as a reducing agent.

Thus, in some embodiments, the ruthenium intermediate obtained from the hydrothermal and/or atmospheric treatment of a ruthenium refinery salt in accordance with the present teachings is reacted with an L-type ligand in the presence of a reducing agent. While neither desiring to be bound by any particular theory nor intending to limit in any measure the scope of the appended claims or their equivalents, it is presently believed that in some embodiments, the yield for the conversion of ruthenium intermediate to ruthenium carbene complex precursor is increased through the addition of a reducing agent. As used herein, the phrase "reducing agent" refers generically to any species capable of reducing another species while itself being oxidized. However, it is to be understood that this capability may or may not actually be a factor in the improved yields observed when a reducing agent is added. In other words, the mechanism by which the reducing agent acts to increase the yield of the conversion of ruthenium intermediate to ruthenium carbene complex precursor may or may not involve oxidation and/or reduction.

In some embodiments, the reacting of the ruthenium intermediate with the L-type ligand and the reducing agent is performed in an alcoholic solvent which, in some embodiments, comprises ethanol. In some embodiments, the reacting of the ruthenium intermediate with the L-type ligand and the reducing agent is performed under reflux conditions in an alcoholic solvent which, in some embodiments, comprises ethanol.

In some embodiments, the reducing agent comprises FeCl$_2$ which, in some embodiments, was observed to increase the 7-hour yield of the reaction between the ruthenium intermediate (NH$_4$)$_2$RuCl$_6$ and COD from about 30% to about 63% at a loading of 1 molar equivalent. For an analogous 24-hour reaction, at a loading of 1 molar equivalent FeCl$_2$, the isolated yield of [Cl$_2$RuCOD]$_x$ from the reaction between (NH$_4$)$_2$RuCl$_6$ and COD was about 89%. Elemental analysis of the [Cl$_2$RuCOD], formed with FeCl$_2$ reducing agent was performed and indicated the presence of about 2% residual Fe in the sample.

Figure 7:
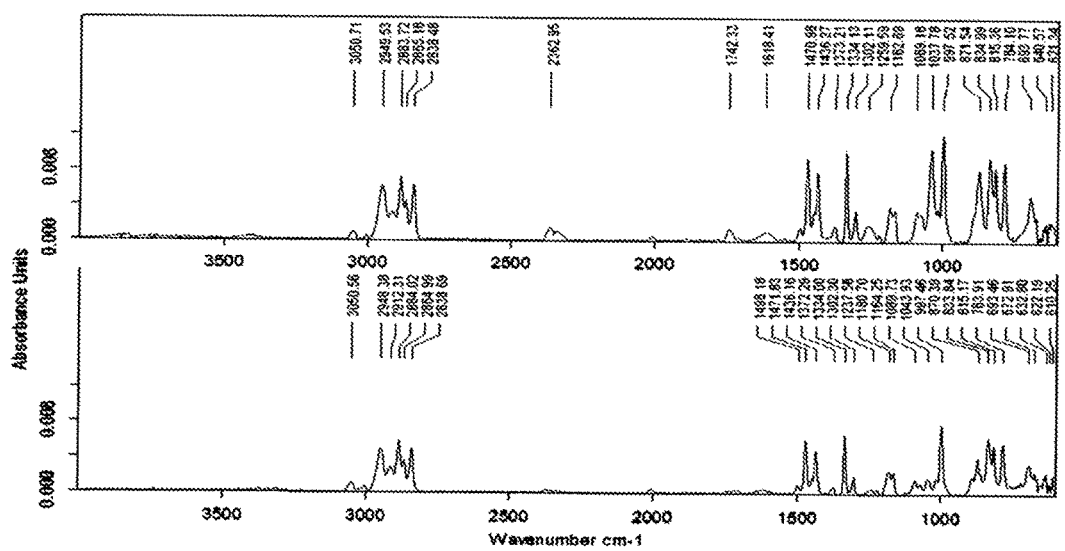
FIG. 7 shows the infrared spectra of (a) [RuCl$_2$(COD)]$_x$ prepared from the reaction of (NH$_4$)$_2$RuCl$_6$, cis,cis-1,5-COD, and FeCl$_2$ reducing agent (top spectrum), and (b) commercially available [RuCl$_2$(COD)]$_x$ purchased from Strem Chemicals, Inc. (bottom spectrum).

Thus, it has been found that the yield for the conversion of (NH$_4$)$_2$RuCl$_6$ to [Cl$_2$RuCOD]$_x$ can be increased from about 62% to about 89% simply by the addition of 1 equivalent of FeCl$_2$. As a result, an overall yield of about 84% can be achieved for the two-step conversion of a ruthenium refinery salt to the ruthenium carbene complex precursor [Cl$_2$RuCOD]$_x$ via the intermediacy of (NH$_4$)$_2$RuCl$_6$. Moreover, as shown in FIG. 7, the ruthenium carbene complex precursor obtained by the reaction involving FeCl$_2$ is spectroscopically very similar to that of [Cl$_2$RuCOD]$_x$ purchased commercially from Strem Chemicals, Inc.

It is to be understood that the reducing agent used in accordance with the present teachings is not restricted, and that all manner of reducing agents are presently contemplated for use. In some embodiments, the reducing agent is organic (e.g., 1,4-CHD, citric acid, ethylene glycol, etc.) In some embodiments, the reducing agent is inorganic. In some embodiments, the reducing agent comprises a metal which, in some embodiments, is selected from the group consisting of Group 7 elements, Group 8 elements, Group 9 elements, Group 10 elements, Group 11 elements, and combinations thereof. In some embodiments, the reducing agent comprises FeCl$_2$. In some embodiments, the reducing agent comprises a hydrated form of FeCl$_2$ (e.g., monohydrated and/or polyhydrated) including but not limited to FeCl$_2$*4H$_2$O. In some embodiments, the reducing agent comprises CoCl$_2$. In some embodiments, the reducing agent comprises a hydrated form of CoCl$_2$ (e.g., monohydrated and/or polyhydrated). In some embodiments, the reducing agent is selected from the group consisting of FeCl$_2$, CoCl$_2$, hydrated forms thereof, and combinations thereof.

In some embodiments, the reducing agent is present at a loading of at least about 1 molar equivalent. In some embodiments, the reducing agent is present at a loading that is greater than 1 molar equivalent. In some embodiments, the reacting of the ruthenium intermediate with the L-type ligand and the reducing agent comprises a reaction time of at least about 5 hours, in some embodiments at least about 10 hours, in some embodiments at least about 15 hours, in some embodiments at least about 20 hours. In some embodiments, the reducing agent comprises $FeCl_2$ and/or a hydrated form thereof, and the L-type ligand comprises a cyclic olefin which, in some embodiments, comprises cyclooctadiene.

A method of preparing an $MX_2L_q$ complex in accordance with the present teachings includes reacting a ruthenium (IV) hexahalo complex that comprises a $[RuX^1{}_yX^2{}_{6-y}]^{2-}$ anion with an L-type ligand and a reducing agent, wherein y is an integer value from 1 to 6. In some embodiments, M comprises ruthenium. In some embodiments, $X^1$ and $X^2$ are halogen atoms that are independently selected from the group consisting of F, Cl, Br, and I.

In some embodiments, the L-type ligand used in the preparation of the $MX_2L_q$ complex is selected from the group consisting of olefins, phosphines, phosphites, amines, CO, $N_2$, and combinations thereof. In some embodiments, the L-type ligand is selected from the group consisting of olefins, phosphines, and a combination thereof. In some embodiments, the L-type ligand comprises a cyclic olefin which, in some embodiments, is selected from the group consisting of a diene, a triene, and a combination thereof. In some embodiments, the cyclic olefin is selected from the group consisting of cyclohexadiene, cycloheptadiene, cyclooctadiene, cyclononadiene, cyclodecadiene, cycloundecadiene, cyclododecadiene, cyclododecatriene, paramenthadiene, phellandrene, norbornadiene, terpinene, limonene, and combinations thereof. In some embodiments, the cyclic olefin is selected from the group consisting of cyclooctadiene, cyclododecatriene, and combinations thereof. In some embodiments, the cyclic olefin comprises 1,5-cyclooctadiene.

In some embodiments, the L-type ligand used in the preparation of the $MX_2L_q$ complex comprises a phosphorous-containing ligand having a structure $PR^1R^2R^3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$ and/or two of $R^1$, $R^2$, and $R^3$ taken together may optionally form a ring with phosphorous. In some embodiments, the phosphorous-containing ligand comprises triphenyl phosphine.

In some embodiments, the reducing agent used in the preparation of the $MX_2L_q$ complex comprises a transition metal which, in some embodiments, is selected from the group consisting of group 8 transition metals, group 9 transition metals, group 10 transition metals, and combinations thereof. In some embodiments, the reducing agent comprises $FeCl_2$. In some embodiments, the reducing agent comprises a hydrated form of $FeCl_2$ including but not limited to $FeCl_2 * 4H_2O$. In some embodiments, the reducing agent comprises $CoCl_2$. In some embodiments, the reducing agent comprises a hydrated form of $CoCl_2$. In some embodiments, the reducing agent is selected from the group consisting of $FeCl_2$, $CoCl_2$, hydrated forms thereof, and combinations thereof.

The following examples and representative procedures illustrate features in accordance with the present teachings, and are provided solely by way of illustration. They are not intended to limit the scope of the appended claims or their equivalents.

EXAMPLES

Materials

Unless otherwise indicated, all chemicals were used as received and without drying. Ruthenium refinery salt was purchased from Refineries A and B. Ethanol (200 proof, absolute), hydrochloric acid (37%), hydrobromic acid (48%), cis,cis-1,5-cyclooctadiene (>98% pure), $FeCl_2$ (Lot no. MKBJ3791V, catalog ID no. 372870) and $CoCl_2$ (Lot no. BCBG0246V, catalog ID no. 232696) were purchased from Sigma Aldrich. $FeCl_2 * 4H_2O$ (Lot no. 20755900, catalog ID no. 93-2632) was purchased from Strem Chemicals, Inc.

Example 1

XRD Analysis of Refinery A Ruthenium Refinery Salt

A sample of a Refinery A ruthenium refinery salt was examined by XRD analysis as received. The x-ray powder patterns were measured (Cu $K_\alpha$ radiation, 5-100° 2θ, 0.0202144° steps, 1 sec/step) on a Bruker D2 Phaser diffractometer equipped with a LynxEye position-sensitive detector. Quantitative analysis of the crystalline phases was carried out by the Rietveld method using GSAS.

The Refinery A ruthenium refinery salt was determined to contain $(NH_4)_4[Ru_2OCl_{10}]$ and 3.9(1) wt % Ru metal impurity. The compound was identified by indexing the pattern on a high-quality body-centered tetragonal unit cell, and using lattice matching techniques to find the K analog (*Acta Cryst. B*, 1979, 35, 558-561). The structure was refined, as shown in Table 1, and hydrogens placed in approximate positions. An acceptable Rietvald refinement was obtained.

TABLE 1

Refined Atom Coordinates of $(NH_4)_4[Cl_5RuORuCl_5]$
Space Group = I 4/m m m
Lattice constants are a = 7.30369(11); b = A; c = 17.0938(4); Alpha = 90; Beta = 90;
Gamma = 90; Cell volume = 911.850(28)

| Name | X | Y | Z | Ui/Ue * 100 | Site sym | Mult | Type | Seq | Fractn |
|---|---|---|---|---|---|---|---|---|---|
| Ru1 | 0.000000 | 0.000000 | 0.10779(18) | 2.14 | 4MM(001) | 4 | RU | 1 | 1.0000 |
| Cl2 | 0.22958(28) | 0.22958(28) | 0.11396(26) | 2.12 | M(+−0) | 16 | CL | 2 | 1.0000 |
| Cl3 | 0.000000 | 0.000000 | 0.24535(44) | 2.12 | 4MM(001) | 4 | CL | 3 | 1.0000 |
| O4 | 0.000000 | 0.000000 | 0.000000 | 3.00 | 4/MMM001 | 2 | O | 4 | 1.0000 |
| N5 | 0.000000 | 0.500000 | 0.250000 | 3.00 | −4M2 001 | 4 | N | 5 | 1.0000 |
| N6 | 0.000000 | 0.500000 | 0.000000 | 3.00 | MMM | 4 | N | 6 | 1.0000 |
| H7 | 0.056070 | 0.433980 | 0.216790 | 5.00 | 1 | | 32 | H | 7 | 0.5000 |
| H8 | 0.060210 | 0.557780 | 0.029880 | 5.00 | 1 | | 32 | H | 8 | 0.5000 |

Example 2

XRD Analysis of Refinery B Ruthenium Refinery Salt

A sample of Refinery B ruthenium refinery salt was first ground with a mortar and pestle prior to analysis but an acceptable powder pattern was not obtained from the damp solid. A portion was ground as an acetone slurry with a mortar and pestle, which resulted in a better powder pattern. The x-ray powder patterns were measured (Cu $K_\alpha$ radiation, 5-100° 2θ, 0.0202144° steps, 1 sec/step) on a Bruker D2 Phaser diffractometer equipped with a LynxEye position-sensitive detector. Quantitative analysis of the crystalline phases was carried out by the Rietveld method using GSAS.

The Refinery B ruthenium refinery salt was determined to contain a mixture of 36.4(2) wt % $(NH_4)_4[Ru_2OCl_{10}]$, 49.6(2) wt % $NH_4Cl$, and 13.9(2) wt % $(NH_4)_2RuCl_5 \cdot H_2O$. The $(NH_4)_4[Ru_2OCl_{10}]$ exhibits significant preferred orientation (texture index=2.02, reflecting difficulty in grinding the large grains to obtain a random powder. The $(NH_4)_2RuCl_5 \cdot H_2O$ was identified by analogy to several $(NH_4)_2RuCl_5X$ compounds. At present, the powder pattern is not yet in the Powder Diffraction File but the crystal structure has been reported (*Zh. Strukt. Khim.*, 2008, 49, 585-588; ICSD collection code 411727). The $(NH_4)_4[Ru_2OCl_{10}]$ in the Refinery B sample exhibits a larger degree of strain broadening than the Refinery A sample.

The phase composition for the Refinery B salt corresponds to a bulk analysis of $C_{0.0}H_{32.51}N_{8.00}O_{0.63}Ru_{1.0}Cl_{11.00}$ compared to the measured $C_{0.09}H_{19.68}N_{5.20}O_{1.30}Ru_{1.0}Cl_{8.43}$. While neither desiring to be bound by any particular theory nor intending to limit in any measure the scope of the appended claims or their equivalents, it is presently believed that the preferred orientation/granularity may have distorted the quantitative analysis and/or that the sample contains some amorphous material.

Example 3

Removal of NH$_4$Cl from Refiner B Ruthenium Refiner Salt by Sublimation

In a sublimator, 7.5 g of Refinery B ruthenium salt was sublimed in vacuo (0.05 Torr), at 150-200° C. for 6 hours. $NH_4Cl$ sublimes onto the cold finger (−5° C.) (2.2 g) while the Ru salts remain below (4.3 g). Ruthenium salt remaining after sublimation is determined to be $(NH_4)_4[Ru_2OCl_{10}]$ and $(NH_4)_2RuCl_5 \cdot H_2O$ by elemental analysis and IR spectroscopy. Ru wt %=32.9%, up from 18.8% in raw salt.

Example 4

Removal of NH$_4$Cl from Refiner B Ruthenium Refiner Salt by Washing with Water To a 150-mL Erlenmeyer flask was added Refinery B ruthenium salt (10.0 g, 49.7% $NH_4Cl$ by mass) and $H_2O$ (20 mL). The slurry immediately turned from black to dark brown and the flask cooled (due—it is presently believed—to endothermic solvation of $NH_4Cl$). The slurry was filtered through a Buchner funnel and washed with $H_2O$ (40 mL). The resulting purified Refinery B salt (4.7 g) was collected.

Example 5

Removal of NH$_4$Cl from Refiner B Ruthenium Refiner Salt by Washing with Ethanol To a 250-mL round-bottomed flask was added Refinery B ruthenium salt (5 g) and ethanol (200 mL). The flask was fitted with a reflux condenser, and the slurry was refluxed for 2 hours at 85° C. The slurry was filtered hot through a Buchner funnel. The recovered solid was washed with ethanol (200 mL). The resulting purified Refinery B salt (2.8 g) was collected.

Example 6

Removal of NH$_4$Cl from Refiner B Ruthenium Refiner Salt b Soxhlet Extraction with Ethanol To the thimble of a Soxhlet extractor was added Refinery B ruthenium salt (25 g, 49.7 NH4Cl by mass). The reservoir of the extractor was filled with ethanol (150 mL), and the extractor heated to 135° C. for 10 hours over 2 days. The Refinery B ruthenium salt was then removed from the thimble, dried, and weighed. Approximately 10 g of the $NH_4Cl$ was removed.

Example 7

Hydrothermal Treatment of Sublimed Refinery B Ruthenium Refinery Salt

In a 23-mL Parr reactor (Part no. 4749), sublimed Refinery B ruthenium refinery salt (1.0660 g) and 6M HCl (10 mL) were heated to 150° C. for 6 hours. The resulting solution was filtered at room temperature and black microcrystals remained on the filter paper. The microcrystals were washed with water. Elemental analysis confirmed that the black microcrystalline product was $(NH_4)_2RuCl_6$ (0.63 g).

Example 8

Preparation of Ruthenium Carbene Complex Precursor [RuCl$_2$(COD)]$_x$ from Refinery B-Derived Ruthenium Intermediate In a 200-mL 3-necked flask fitted with an inlet, a condenser, a bubbler, and a stopper, $(NH_4)_2RuCl_6$ (1.57 g, product from hydrothermal treatment of a Refinery B salt), cis,cis-1,5-cyclooctadiene (1.48 g, 3 eq.), and ethanol (45 mL) were refluxed for 6 hours under $N_2$. The solid was insoluble in ethanol; however, there was a color change from black to rusty brown. The solid was filtered at ambient temperature through a Buchner funnel and washed with ethanol. The isolated rusty brown solid was then washed with $H_2O$ (100 mL) yielding a yellowish brown solid, $[RuCl_2(COD)]_x$ (0.2126 g).

Example 9

Hydrothermal Treatment of Refinery A Ruthenium Refinery Salt

In a 23-mL Parr reactor, Refinery A ruthenium refinery salt (1 g) and 6M HCl (10 mL) were heated to 150° C. for 6 hours. The resulting solution was filtered at room temperature and black microcrystals remained on the filter paper. The microcrystals were washed with water. Elemental analysis confirmed that the black microcrystalline product was $(NH_4)_2RuCl_6$ (0.6 g).

Example 10

Hydrothermal Treatment of Refinery A Ruthenium Refinery Salt

In a 23-mL Parr reactor, Refinery A ruthenium refinery salt (1 g) and 9M HCl (5 mL) were heated to 150° C. for 2 hours. The resulting solution was filtered at room temperature and black microcrystals remained on the filter paper. The microcrystals were washed with acetone. Elemental analysis confirmed that the black microcrystalline product was $(NH_4)_2RuCl_6$ (1.1 g).

Example 11

Atmospheric Treatment of Refinery A Ruthenium Refinery Salt

In a 100-mL round-bottomed flask fitted with a condenser, Refinery A ruthenium refinery salt (3.0302 g) and concentrated HCl (37%, 30 mL) were refluxed at 100° C. for 6 hours. The resulting solution was filtered at room temperature in a Buchner funnel, and a fine black solid, $(NH_4)_2RuCl_6$ (2.5118 g) was washed with water and recovered from the filter paper.

Example 12

Atmospheric Treatment of Refinery A Ruthenium Refinery Salt

In a 200-mL 3-necked flask fitted with $N_2$ purge and a condenser, Refinery A ruthenium refinery salt (5 g) and concentrated HBr (50 mL) were refluxed for 6 h. A bluish-black solid (7.6 g) was filtered out of the solution at room temperature using a Buchner funnel and washed with acetone. Elemental analysis confirmed that a majority of the solid product is $(NH_4)_2RuBr_6$ (yield about 80%) with about 1.2 wt % chlorine present. The chlorine may stem from a small amount of $(NH_4)_2RuCl_6$ $(NH_4)_2RuCl_zBr_{6-z}$, where z is an integer from 1 to 5, and/or from unreacted $(NH_4)_4$ $[Ru_2OCl_{10}]$ starting material present in the sample.

Example 13

Preparation of Ruthenium Carbene Complex Precursor $[RuCl_2(COD)]_x$ from Refinery A-Derived Ruthenium Intermediate In a 200-mL 3-necked flask fitted with an inlet, a condenser, a bubbler, and a stopper, $(NH_4)_2RuCl_6$ (1.13 g, product from hydrothermal treatment of a Refinery A salt), cis,cis-1,5-cyclooctadiene (1.05 g, 3 eq.), and ethanol (30 mL) were refluxed for 6 hours under $N_2$. The solid was insoluble in ethanol; however, there was a color change from black to rusty brown. The solid was filtered at ambient temperature through a Buchner funnel and washed with ethanol. The isolated rusty brown solid was then washed with $H_2O$ (100 mL) yielding a yellowish brown solid, $[RuCl_2(COD)]_x$ (0.2977 g).

Figure 6:
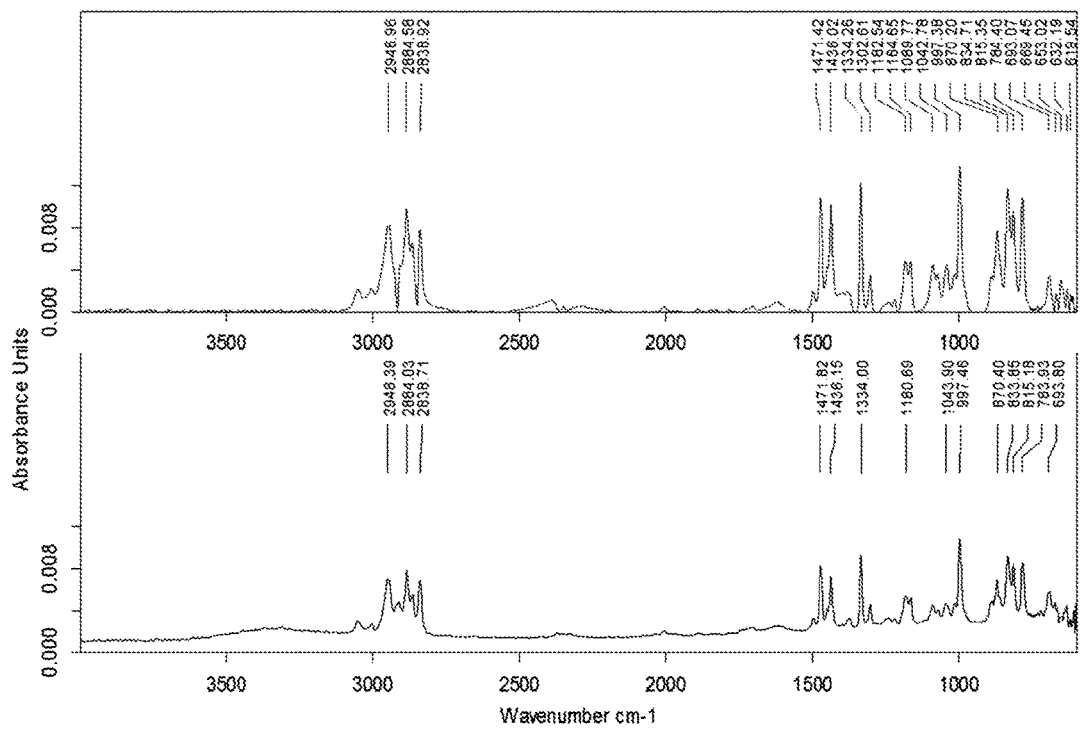
FIG. 6 shows the infrared spectra of (a) [RuCl$_2$(COD)]$_x$ prepared from the reaction of (NH$_4$)$_2$RuCl$_6$ and cis,cis-1,5-COD (top spectrum), and (b) commercially available [RuCl$_2$(COD)]$_x$ purchased from Strem Chemicals, Inc. (bottom spectrum).

As shown in FIG. 6, the IR spectrum of synthesized $[RuCl_2(COD)]_x$ (top spectrum) prepared from a Refinery A salt as described above matches that of commercially available $[RuCl_2(COD)]_x$ from Strem Chemicals, Inc. (Newburyport, Mass.) (bottom spectrum). Moreover, an equivalent product is obtained when the $[RuCl_2(COD)]_x$ is prepared from Refinery B salt (after its purification via sublimation). Thus, a viable synthesis of $[RuCl_2(COD)]_x$—a precursor to ruthenium carbene complexes, such as those used as catalysts in olefin metathesis—from low-cost ruthenium refinery salts via the intermediacy of $(NH_4)_2RuCl_6$ has been demonstrated.

Example 14

Preparation of Ruthenium Carbene Complex Precursor $[RuCl_2(COD)]_x$ from Refinery A-Derived Ruthenium Intermediate In a 200-mL 3-necked flask fitted with an inlet, a condenser, a bubbler, and a stopper, $(NH_4)_2RuCl_6$ (3.03 g, product from hydrothermal treatment of a Refinery A salt), cis,cis-1,5-cyclooctadiene (1.96 g, 2 eq.), and ethanol (45 mL) were refluxed for 30 hours under $N_2$. The solid was insoluble in ethanol; however, there was a color change from black to rusty brown. The solid was filtered at ambient temperature through a Buchner funnel and washed with ethanol. The isolated rusty brown solid was then washed with $H_2O$ (250 mL) yielding a yellowish brown solid, $[RuCl_2(COD)]_x$ (1.56 g).

Example 15

XRD Analysis of Ruthenium Intermediates Obtained from Hydrothermal and Atmospheric Treatments of Refinery A Ruthenium Refinery Salt A sample of a ruthenium intermediate obtained from the atmospheric treatment of a Refinery A salt was examined by XRD analysis as received. A sample of a ruthenium intermediate obtained from the hydrothermal treatment of a Refinery A salt was ground with a mortar and pestle prior to analysis.

The x-ray powder patterns were measured (Cu $K_\alpha$ radiation, 5-100° 2θ, 0.0202144° steps, 0.5 sec/step) on a Bruker D2 Phaser diffractometer equipped with a LynxEye position-sensitive detector. Quantitative analysis of the crystalline phases was carried out by the Rietveld method using GSAS.

The x-ray powder pattern of the major phase in both samples matches that of several face-centered cubic $(NH_4)_2MCl_6$ compounds. Accordingly, this phase was identified as $(NH_4)_2RuCl_6$. Since the crystal structure of $(NH_4)_2RuCl_6$ was not previously refined, although some of its thermodynamic properties have been reported in the literature (*J. Chem Thermodynamics*, 2002, 34, 133-153), the structure of $(NH_4)_2ReCl_6$ was used as the initial model for the refinement, as shown in Table 2.

TABLE 2

| Refined Crystal Structure of $(NH_4)_2RuCl_6$ Space Group = Fm3m, a = 9.86201 (13) Å | | | | |
|---|---|---|---|---|
| ATOM | x | y | z | $U_{iso}$, Å$^2$ |
| Ru1 | 0 | 0 | 0 | 0.0241(7) |
| Cl2 | 0.2361(2) | 0 | 0 | 0.0255(8) |
| N3 | ¼ | ¼ | ¼ | 0.03 |
| H4 | 0.3072 | 0.3072 | 0.3072 | 0.039 |

The displacement coefficient of the Cl is reasonable for a fully-occupied chlorine atom. Therefore, the compound is identified as $(NH_4)_2RuCl_6$ rather than $(NH_4)_2RuCl_5 \cdot H_2O$, which would yield a larger $U_{iso}$ for the Cl.

The phase composition data for the two samples are shown in Table 3. Both samples are comprised primarily of $(NH_4)_2RuCl_6$ but contain varying amounts of impurities including $(NH_4)_4[Ru_2OCl_{10}]$ and Ru metal. The hydrothermally-derived ruthenium intermediate has a lower concentration of impurities and was contains 94.3 wt % $(NH_4)_2RuCl_6$, 0.9 wt % $(NH_4)_4[Ru_2OCl_{10}]$, and 4.9 wt % Ru metal. The atmospherically-derived ruthenium intermediate appears to have some amorphous material (from a broad feature in the background at approximately 16° 2θ), and contains 83.5 wt % $(NH_4)_2RuCl_6$, 10 wt % $(NH_4)_4[Ru_2OCl_{10}]$, and 6.4 wt % Ru metal.

TABLE 3

Phase Compositions of Ruthenium Intermediate Samples

|  | Hydrothermally-Derived Ruthenium Intermediate | Atmospherically-Derived Ruthenium Intermediate |
|---|---|---|
| $(NH_4)_2RuCl_6$, wt % | 94.3(1) | 83.5(1) |
| a, Å | 9.8637(2) | 9.8620(1) |
| Profile U | 17.2(49) | 51(3) |
| Profile Y | 16.4(4) | 4.8(4) |
| strain, % | 0.25(1) | 0.05(1) |
| $(NH_4)_4[Ru_2OCl_{10}]$, wt % | 0.9(1) | 10.0(1) |
| Ru, wt % | 4.9(1) | 6.4(1) |
| Profile X | 5.8(3) | 6.3(2) |
| size, Å | 2500(200) | 2200(100) |
| other |  | amorphous |

Example 16

General Procedure for Preparation of Ruthenium Carbene Complex Precursor $[RuCl_2(COD)]_x$ from Ruthenium Intermediate and Reducing Agent In a 100-mL, 3-necked flask fitted with a $N_2$-purge and a condenser, $(NH_4)_2RuCl_6$ (1 g), cis,cis-1,5-COD (2 eq.), reducing agent (1 eq.) and EtOH (25 mL) are refluxed for 7 hours. The reaction solution is then filtered through a Buchner funnel, and the filtrate is washed with EtOH. The solid is collected from the filter paper, washed with $H_2O$, and refiltered. The resultant solid is then washed with additional $H_2O$ until the wash is clear and rinsed with acetone (10 mL). The products are analyzed by IR.

Example 17

Preparation of Ruthenium Carbene Complex Precursor $[RuCl_2(COD)]_x$ from Refinery A-Derived Ruthenium Intermediate and $FeCl_2$ Reducing Agent In a 100-mL, 3-necked flask fitted with an inlet, a condenser, a bubbler, and a stopper, $(NH_4)_2RuCl_6$ (2.0331 g, product from hydrothermal treatment of a Refinery A salt), cis,cis-1,5-COD (1.60 mL, 2 eq.) $FeCl_2$ (0.7580 g, 1 eq.), and ethanol (40 mL) were refluxed for 24 hours under $N_2$. The solid was not soluble in ethanol; however, there was a color change from black to rusty brown. The solid was filtered at ambient temperature through a Buchner funnel and washed with ethanol. The isolated rusty brown solid was then washed with $H_2O$ (500 mL) yielding $[Cl_2RuCOD]_x$ as a rusty orange solid (1.4520 g, yield=89%).

Example 18

Preparation of Ruthenium Carbene Complex Precursor $[RuCl_2(COD)]_x$ from Refinery A-Derived Ruthenium Intermediate and $CoCl_2$ Reducing Agent In a 100-mL, 3-necked flask fitted with an inlet, a condenser, a bubbler, and a stopper, $(NH_4)_2RuCl_6$ (0.9819 g, product of hydrothermal treatment of a Refinery A salt), cis,cis-1,5-COD (0.7 mL, 2 eq.), $CoCl_2$ (0.37, 1 eq.), and ethanol (25 mL) were refluxed for 7 hours under $N_2$. The $(NH_4)_2RuCl_6$ was not soluble in ethanol; however, there was a color change from black to brown (in a teal solution). The solid was filtered at ambient temperature through a Buchner funnel and washed with ethanol. The isolated brown solid was then washed with $H_2O$ (250 mL) yielding $[Cl_2RuCOD]_x$ as a rusty orange solid (0.3892 g, yield=48.7% in 7 hours).

Example 19

Preparation of Ruthenium Carbene Complex Precursor $[RuCl_2(COD)]_x$ from Refinery A-Derived Ruthenium Intermediate and $FeCl_2 \cdot 4H_2O$ Reducing Agent In a 100-mL, 3-necked flask fitted with an inlet, a condenser, a bubbler, and a stopper, $(NH_4)_2RuCl_6$ (1.0116 g, product of hydrothermal treatment of a Refinery A salt), cis,cis-1,5-COD (0.7 mL, 2 eq.), $FeCl_2 \cdot 4H_2O$ (0.5914 g, 1 eq.), and ethanol (25 mL) were refluxed for 7 hours under $N_2$. The $(NH_4)_2RuCl_6$ was not soluble in ethanol; however, there was a color change from black to rusty brown. The solid was filtered at ambient temperature through a Buchner funnel and washed with ethanol. The isolated rusty brown solid was then washed with $H_2O$ (250 mL) yielding $[Cl_2RuCOD]_x$ as a rusty orange solid (0.4913 g, yield=60.7% in 7 hours).

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method of preparing an $MX_2L_q$ complex comprising:
reacting a ruthenium (IV) hexahalo complex that comprises a $[RuX^1{}_yX^2{}_{6-y}]^{2-}$ anion with an L-type ligand in the presence of a reducing agent to form an $MX_2L_q$ complex;
wherein M comprises ruthenium;
wherein $X^1$ and $X^2$ are halogen atoms that are independently selected from the group consisting of Cl and Br;
wherein y is an integer value from 1 to 6; and
wherein q is 3.

2. The invention of claim 1 wherein the L-type ligand is selected from the group consisting of olefins, phosphines, phosphites, amines, CO, $N_2$, and combinations thereof.

3. The invention of claim 1 wherein the L-type ligand is selected from the group consisting of olefins, phosphines, and a combination thereof.

4. The invention of claim 1 wherein the L-type ligand comprises a cyclic olefin.

5. The invention of claim 4 wherein the cyclic olefin is selected from the group consisting of a diene, a triene, and a combination thereof.

6. The invention of claim 4 wherein the cyclic olefin is selected from the group consisting of cyclohexadiene, cycloheptadiene, cyclooctadiene, cyclononadiene, cyclodecadiene, cycloundecadiene, cyclododecadiene, cyclododecatriene, paramenthadiene, phellandrene, norbornadiene, terpinene, limonene, and combinations thereof.

7. The invention of claim 4 wherein the cyclic olefin is selected from the group consisting of cyclooctadiene, cyclododecatriene, and combinations thereof.

8. The invention of claim 4 wherein the cyclic olefin comprises 1,5-cyclooctadiene.

9. The invention of claim 1 wherein the L-type ligand comprises a phosphorous-containing ligand having a structure $PR^1R^2R^3$;
wherein $R^1, R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
wherein covalent bonds may optionally exist between two or more of $R^1$, $R^2$, and $R^3$ and wherein any two of $R^1$, $R^2$, and $R^3$ taken together may optionally form a ring with the phosphorous atom.

10. The invention of claim 9 wherein the phosphorous-containing ligand comprises triphenyl phosphine.

11. The invention of claim 1 wherein the reducing agent is inorganic.

12. The invention of claim 1 wherein the reducing agent comprises $FeCl_2$ or a hydrated form thereof.

13. The invention of claim 1 wherein the reducing agent comprises $CoCl_2$ or a hydrated form thereof.

14. The invention of claim 1 wherein the reducing agent is organic.

15. The invention of claim 1 wherein the reacting of the ruthenium intermediate with the L-type ligand and the reducing agent is performed in an alcoholic solvent.

16. The invention of claim 15 wherein the alcoholic solvent comprises ethanol.

17. The invention of claim 1 wherein the reducing agent comprises $FeCl_2$, and wherein the L-type ligand comprises a cyclic olefin.

18. The invention of claim 17 wherein the cyclic olefin comprises cyclooctadiene.

19. The invention of claim 1 wherein the ruthenium (IV) hexahalo complex further comprises an ammonium cation and wherein y is 6.

20. The invention of claim 1 wherein the ruthenium (IV) hexahalo complex comprises $(NH_4)_2RuCl_6$.

* * * * *